(12) United States Patent
Pearce

(10) Patent No.: US 7,138,079 B2
(45) Date of Patent: Nov. 21, 2006

(54) METHODS FOR MAKING FOAMED ELASTOMER GELS

(75) Inventor: Terry V. Pearce, Alpine, UT (US)

(73) Assignee: EdiZone, LC, Alpine, UT (US)

( * ) Notice: Subject to any disclaimer, the term of this patent is extended or adjusted under 35 U.S.C. 154(b) by 62 days.

(21) Appl. No.: 10/364,903

(22) Filed: Feb. 11, 2003

(65) Prior Publication Data
US 2003/0236313 A1 Dec. 25, 2003

Related U.S. Application Data

(60) Provisional application No. 60/356,279, filed on Feb. 11, 2002.

(51) Int. Cl.
*B29C 44/02* (2006.01)
(52) U.S. Cl. ............... 264/50; 264/51; 264/54; 264/101; 264/102
(58) Field of Classification Search ........... 264/50, 264/51, 54, 101, 102
See application file for complete search history.

(56) References Cited

U.S. PATENT DOCUMENTS

| | | | | |
|---|---|---|---|---|
| 3,812,225 A | * | 5/1974 | Hosoda et al. ............. 264/54 |
| 3,959,434 A | * | 5/1976 | Squier ................. 264/45.8 |
| 4,369,284 A | | 1/1983 | Chen .................... 524/476 |
| 4,618,213 A | | 10/1986 | Chen .................. 350/96.34 |
| 5,153,254 A | | 10/1992 | Chen .................... 524/505 |
| 5,239,723 A | | 8/1993 | Chen ................. 15/104.002 |
| 5,262,468 A | | 11/1993 | Chen .................... 524/476 |
| 5,278,220 A | | 1/1994 | Vermeire et al. ......... 524/490 |
| 5,324,222 A | | 6/1994 | Chen ..................... 446/34 |
| 5,334,646 A | | 8/1994 | Chen .................... 524/474 |
| 5,336,708 A | | 8/1994 | Chen .................... 524/474 |
| 5,391,337 A | * | 2/1995 | Kearney et al. ........... 264/51 |
| 5,421,874 A | | 6/1995 | Pearce ................... 106/122 |
| 5,475,890 A | | 12/1995 | Chen ................. 15/104.002 |
| 5,508,334 A | | 4/1996 | Chen .................... 524/474 |
| 5,549,743 A | | 8/1996 | Pearce ................... 106/122 |
| 5,592,706 A | | 1/1997 | Pearce ..................... 5/654 |
| 5,624,294 A | | 4/1997 | Chen .................... 446/253 |
| 5,626,657 A | | 5/1997 | Pearce ................... 106/122 |
| 5,633,286 A | | 5/1997 | Chen .................... 524/474 |
| 5,655,947 A | | 8/1997 | Chen ..................... 446/46 |
| 5,749,111 A | | 5/1998 | Pearce ..................... 5/652 |
| 5,760,117 A | | 6/1998 | Chen .................... 524/270 |
| 5,829,081 A | | 11/1998 | Pearce .................... 65/654 |
| 5,868,597 A | | 2/1999 | Chen ..................... 446/46 |
| 5,881,409 A | | 3/1999 | Pearce ..................... 5/702 |
| 5,884,639 A | | 3/1999 | Chen .................... 132/321 |
| 5,938,499 A | | 8/1999 | Chen .................... 446/253 |
| 5,962,572 A | | 10/1999 | Chen .................... 524/474 |
| 5,991,960 A | | 11/1999 | Johnson ................ 15/210.1 |
| 5,994,450 A | | 11/1999 | Pearce ................... 524/505 |
| 6,020,055 A | | 2/2000 | Pearce ................... 428/323 |
| 6,026,527 A | | 2/2000 | Pearce ..................... 5/654 |
| 6,033,283 A | | 3/2000 | Chen .................... 446/253 |
| 6,050,871 A | | 4/2000 | Chen ..................... 446/46 |
| 6,099,951 A | | 8/2000 | Flick et al. ............. 428/306.6 |
| 6,117,176 A | | 9/2000 | Chen ..................... 623/36 |
| 6,148,830 A | | 11/2000 | Chen .................... 132/321 |

(Continued)

Primary Examiner—Allan R. Kuhns
(74) Attorney, Agent, or Firm—Daniel McCarthy

(57) ABSTRACT

Methods for making foamed elastomer gels are disclosed. Chemical foaming agents may be incorporated or gas may be injected into a molten gel and then using heating and cooling techniques and/or additives, gas bubbles are formed and preserved in the cooled and solidified elastomer gel.

45 Claims, 3 Drawing Sheets

U.S. PATENT DOCUMENTS

| | | | |
|---|---|---|---|
| 6,152,137 A | 11/2000 | Schwartz et al. | 128/846 |
| 6,161,555 A | 12/2000 | Chen | 132/321 |
| 6,186,906 B1 | 2/2001 | Sullivan et al. | 473/351 |
| 6,187,837 B1 | 2/2001 | Pearce | 523/105 |
| 6,200,284 B1 | 3/2001 | Flick | 602/13 |
| 6,231,941 B1 * | 5/2001 | Cundiff et al. | 428/36.3 |
| 6,324,703 B1 | 12/2001 | Chen | 2/458 |
| 6,333,374 B1 | 12/2001 | Chen | 524/270 |
| 6,413,455 B1 * | 7/2002 | Yates | 264/51 |
| 6,413,458 B1 | 7/2002 | Pearce | 264/141 |
| 6,420,475 B1 | 7/2002 | Chen | 524/505 |
| 6,447,865 B1 | 9/2002 | Flick et al. | 428/52 |
| 6,498,198 B1 | 12/2002 | Pearce | 521/54 |

* cited by examiner

METHODS FOR MAKING FOAMED ELASTOMER GELS

CROSS REFERENCE TO RELATED APPLICATIONS

PRIORITY: I hereby claim the benefit under Title 35, U.S.C. § 119(e) of a U.S. Provisional Patent Application filed on Feb. 11, 2002 and having Ser. No. 60/356,279.

BACKGROUND

Elastomer gel materials, such as those made from KRATON® or SEPTON® A-B-A triblock copolymer elastomer-extended with mineral or other oils, are well known. Those gel materials can be foamed, such as by use of chemical foaming agents. Such foaming is disclosed in some of the cases to which priority is claimed above. Those gel materials may also be foamed by injecting a gas, such as carbon dioxide or nitrogen, under high pressure so that the elastomer gel dissolves. When pressure on the gel is reduced, gas bubbles from the injected gas form and remain in it, leaving an elastomer gel that is instantly foamed.

Foam created using elastomer gels has excellent qualities including but not limited to feel and durability. In addition, such foams can be recycled more readily than ordinary thermoset polyurethane foams because the elastomer foams are thermoplastic in nature. One problem that may be encountered in making elastomer foam in commercially-viable thicknesses is that the low viscosity of the melted elastomer gel allows the bubbles, which create the cells in the finished foam, to coalesce or to migrate out of the melt before the melt can be sufficiently solidified by cooling. Elastomer foams without additives can readily be made in very thin layers, up to about 4 millimeters thick, because the melt can be cooled before the bubble distribution is lost. Commercial applications for 4 millimeter or less thick foam are limited, and many more applications exist for thicker foams.

SUMMARY

Methods for making foamed elastomer gels are disclosed.

DETAILED DESCRIPTION

Figure 1:
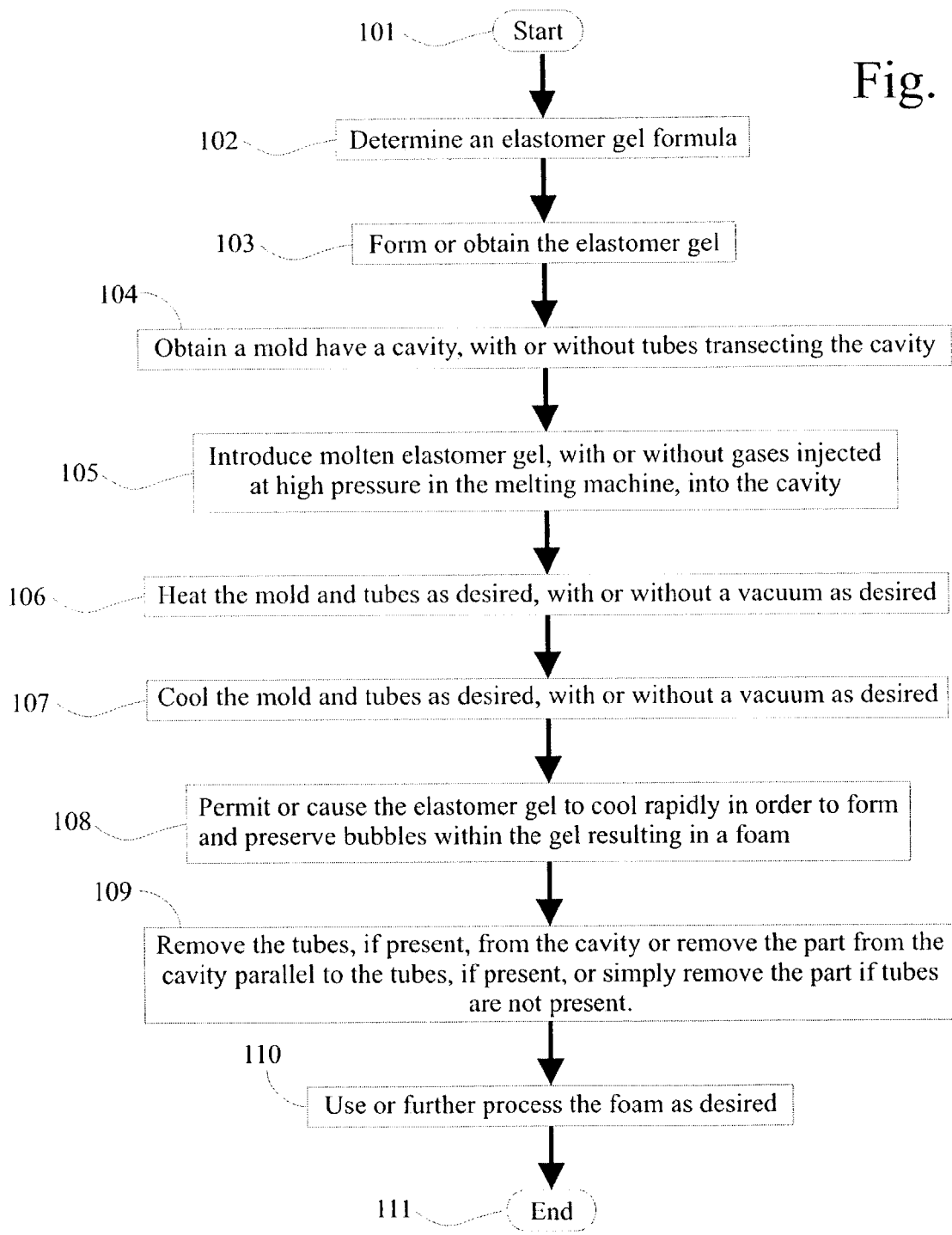
FIGS. 1–3 depict methods for making a gel foam.

Several methods are disclosed that can be used singly or in combination to manufacture elastomer gel foams in thicknesses suitable for commercial applications, without limitation, up to 1.5 meter thick or even thicker. Elastomer gel as used herein shall mean any elastomer gel as exemplified by gels of the several patents and patent applications to which priority is cited above, and others which may be known or become known at a later date. As an example, such gels may include combination of an elastomer and a plasticizer. The elastomer may be any appropriate elastomer, including but not limited to A-B-A triblock copolymers such as SEPS, SEBS, SEEPS and others. Suitable plasticizers include oils such as mineral oils, resins, rosins, and others. Other components may be used in the gel as well, such as antioxidants, colorants, bleed reducing additives, microspheres and other components.

An example elastomer gel that can be considered for discussion purposes herein includes, in parts by weight:

EXAMPLE ELASTOMER GEL FORMULA

| | |
|---|---|
| 20 parts | Septon 4055 SEPS tri-block copolymer, available from Kurary of Japan |
| 60 parts | Duoprime 90 white paraffinic mineral oil available from Lyondell of Houston, Texas |
| 0.3 parts | blaze orange aluminum lake pigment available from Day-Glo Corporation of Twinsburg, Ohio |
| 0.1 parts | Irganox 1076 antioxidant available from Ciba Geigy of Basel, Switzerland |

Foaming of the elastomer gel can be according to one or more of the steps disclosed below. An elastomer gel is prepared according to the desired formulation. The elastomer gel preparation may be simply blended ingredients or may be melted and solidified by cooling into a homogenous compound in a form suitable for introduction into an extruder, an injection molding machine, or other such plastics machine.

A mold is selected that can be heated and cooled rapidly. The mold has a cavity for forming an elastomer gel into a desired shape, and the mold may or may not contain tubes or rods that transect the finished foamed elastomer cavity.

The elastomer gel preparation mentioned above is then melted and the molten elastomer gel is extruded, injected, forced, compressed or placed into the mold cavity and cooled or permitted to cool to form a foamed elastomer gel. The gases which form the bubbles that convert the elastomer gel into elastomer gel foam are created within the molten gel by use of chemical foaming agents in the formulation or by injection of gases at high pressure during the melting process, without limitation may be an extruder machine.

Alternately, the elastomer gel preparation mentioned above can be melted and injected into a mold in the normal manner of injection molding,-using a formulation that allows the elastomer gel to be molded without initiating the chemical foaming agent selected for said formulation. The injection molded elastomer gel part, which is not foamed, is then placed in an oven for an appropriate duration at a temperature that will activate the foaming agent and soften the elastomer gel sufficiently to allow the formation of bubbles to deform the elastomer gel, thus making the foam durable, but at a sufficiently short duration and a sufficiently low temperature to avoid migration of bubbles from the site at which the bubbles formed thus preserving the desirable qualities of the elastomer gel foam. The elastomer gel part may or may not have holes partially or fully transecting the part to aid in uniformly heating, initiating the chemical foaming agent, and cooling the part.

The mold and tubes or rods, if present, mentioned above can be heated and cooled rapidly by means of fluid moving through them or by other means as desired. The mold and tubes or rods can be heated if necessary for the type of foam being produced prior to the melted gel being introduced into the mold cavity. If necessary to the type of foam and foaming agent or foaming method, the mold can be held at the heated temperature until the bubbles obtain the size and distribution within the melted gel as desired whereupon the mold and tubes or rods can be rapidly cooled, cooling in turn the foam before the bubbles can migrate away from the desired even distribution throughout the gel.

For combinations of gel formulations and foaming methods or agents that do not require the mold to keep the melted gel at a high temperature, the foamed gel can be cooled as soon as it is placed in the mold by rapidly cooling the mold and tubes or rods, if present, as above.

When the elastomer gel and distributed gas-filled small bubbles within the mold cavity are permitted to cool, an elastomer gel with gas bubbles within it is formed. This is referred to as a 'foam'. When the foam is sufficiently cooled, the tubes or rods, if present, can be withdrawn from the foam so the foam can be removed from the cavity or the foam can be withdrawn from the cavity parallel to the tubes or rods.

A vacuum can be advantageously applied to the mold described above in order to assist in maintaining even bubble distribution within the elastomer gel during cooling. The vacuum level can be increased and decreased during the molding cycle as necessary to optimize the quality of the foam. Vacuum levels from only a few millimeters of mercury to full vacuum are effective depending on the gel formulation and the foaming method.

Alternately elastomer gel foam can be made in bulk form without the use of a mold. The elastomer gel formulation can be prepared, melted, and extruded onto a moving conveyor belt. Bubbles within the elastomer gel can be generated from chemical foaming agents, in which case the moving conveyor belt may or may not move the elastomer gel through a heated oven to allow initiation of the chemical foaming agent before the elastomer gel foam is cooled, or the bubbles may be formed from gases injected into the molten elastomer gel under high pressure, without limitation typically in an extruder machine in which case the elastomer gel foam can be cooled immediately, without need for moving through a heating oven.

Stability-inducing additives such as fatty acids, stearamides, or stearyl stearamides including but not limited to Kemamide S, can be added to the gel prior to foaming resulting in significantly higher stability in bubble distribution in the melted gel. Example ranges of such additives include 0.5% to 10%, or about 4%, or other amounts found to have a positive impact on the finished foam.

A surfactant can be added to the gel resulting in significantly higher stability in bubble distribution in the melted gel. Example ranges of surfactants include 1% to 5%, or about 2%, or other amounts found to have a positive impact on the finished foam. Example surfactants that may be considered for use in the gel include Zonyl FSG, aliphatic carboxylic acids such as lauric acid, myristic acid, palmitic acid, stearic acid, and oleic acid; fatty acid soaps such as sodium salts or potassium salts of the above aliphatic carboxylic acids; N-acyl-N-methylglycine salts, N-acyl-N-methyl-.beta.-alanine salts, N-acylglutamic acid salts, polyoxyethylene alkyl ether carboxylic acid salts, acylated peptides, alkylbenzenesulfonic acid salts, alkylnaphthalenesulfonic acid salts, naphthalenesulfonic acid salt-formalin polycondensation products, melaminesulfonic acid salt-formalin polycondensation products, dialkylsulfosuccinic acid ester salts, alkyl sulfosuccinate disalts, polyoxyethylene alkylsulfosuccinic acid disalts, alkylsulfoacetic acid salts, (.alpha.-olefinsulfonic acid salts, N-acylmethyltaurine salts, sodium dimethyl 5-sulfoisophthalate, sulfated oil, higher alcohol sulfuric acid ester salts, polyoxyethylene alkyl ether sulfuric acid salts, secondary higher alcohol ethoxysulfates, polyoxyethylene alkyl phenyl ether sulfuric acid salts, monoglysulfate, sulfuric acid ester salts of fatty acid alkylolamides, polyoxyethylene alkyl ether phosphoric acid salts, polyoxyethylene alkyl phenyl ether phosphoric acid salts, alkyl phosphoric acid salts, sodium alkylamine oxide bistridecylsulfosuccinates, sodium dioctylsulfosuccinate, sodium dihexylsulfosuccinate, sodium dicyclohexylsulfosuccinate, sodium diamylsulfosuccinate, sodium diisobutylsulfosuccinate, alkylamine guanidine polyoxyethanol, disodium sulfosuccinate ethoxylated alcohol half esters, disodium sulfosuccinate ethoxylated nonylphenol half esters, disodium isodecylsulfosuccinate, disodium N-octadecylsulfosuccinamide, tetrasodium N-(1,2-dicarboxyethyl)-N-octadecylsulfosuccinamide, disodium mono- or didodecyldiphenyl oxide disulfonates, sodium diisopropylnaphthalenesulfonate, and neutralized condensed products from sodium naphthalenesulfonate.

Emulsifiers including but not limited to mono and diglycerides such as Witconol 150 or Witconol 124, can be added to the gel resulting in significantly higher stability in bubble distribution in the melted gel. Example ranges of such emulsifiers include 1% to 10%, about 4%, or other amounts found to have a positive impact on the finished foam.

FIG. 1 depicts an example flow chart of steps that may be used in carrying out methods for making a foamed elastomer gel in a mold cavity as disclosed herein. Steps include start 101, determining an appropriate elastomer gel formula or desired characteristics 102, and forming or obtaining the elastomer gel preparation 103. Then a mold with heating/cooling functions is created or obtained as described above that may or may not have heating/cooling tubes or rods that transect the mold cavity 104. Molten elastomer containing chemical foaming agents or injected gases is introduced into the mold cavity 105. The mold and tubes or rods, if present, may be heated 106 and/or cooled 107 as desired in order to facilitate forming and retaining gas bubbles in the gel. A vacuum may be applied to the gel in 106 or 107 as desired to influence the resulting foam. The molten elastomer gel is either actively cooled or permitted to cool 108 rapidly in order to solidify the gel, form a foam and preserve bubbles within the foam. Tubes or rods, if present, are removed from the cavity, or the foam is removed from the cavity parallel to the tubes or rods, if present, or the foam is simply removed from the cavity if no tubes or rods are present 109. The foam is solid and non-flowable at room temperature and may be handled. Then the foam may be used as is or further processed 110 such as in a manufactured article, ending 111 the process.

Figure 2:
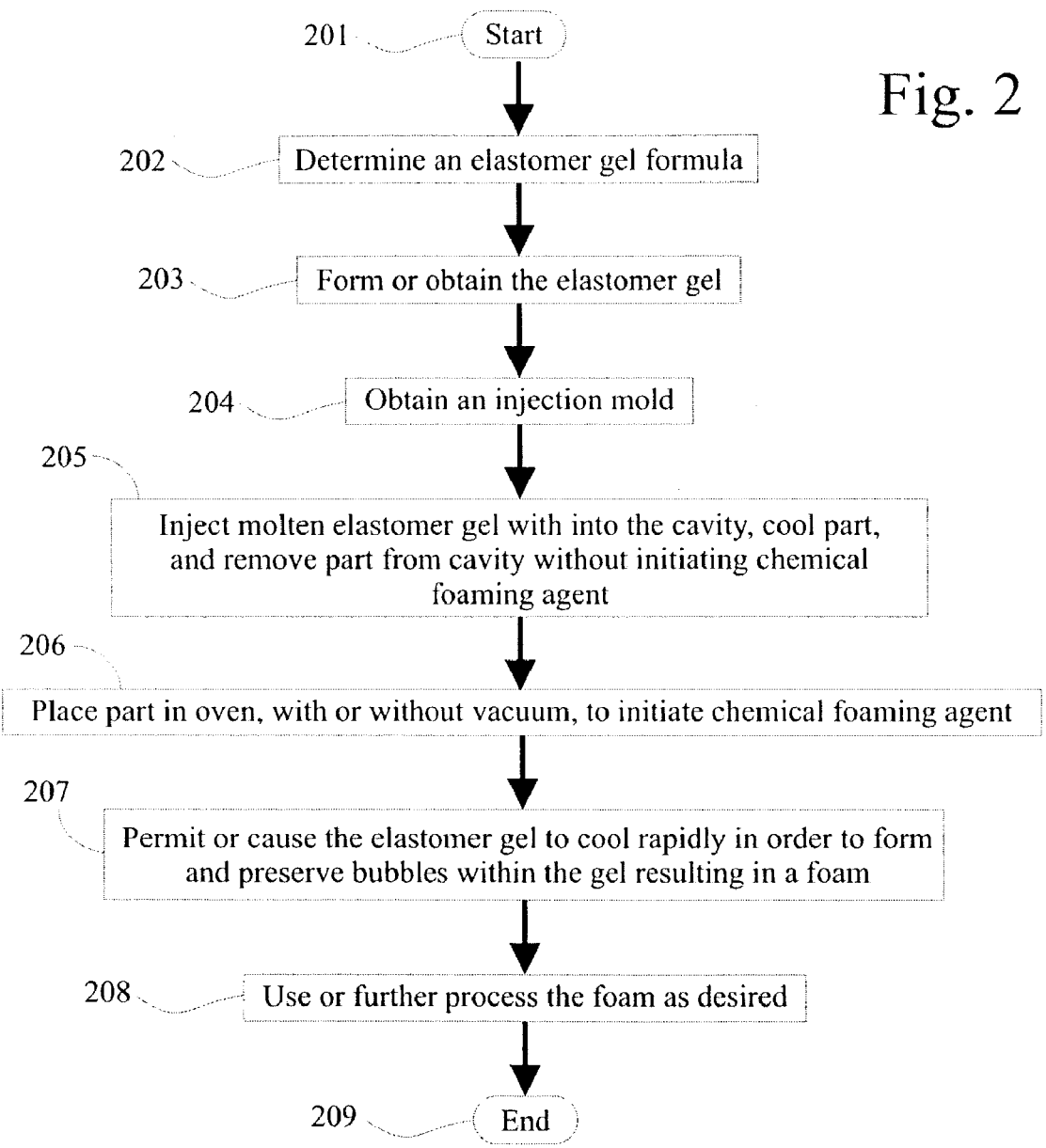

FIG. 2 depicts an example flow chart of steps that may be used in carrying out methods for making a foamed elastomer gel by injection molding unfoamed elastomer parts containing uninitiated chemical foaming agents that are subsequently heated to create the foam as disclosed herein. Steps include start 201, determining an appropriate elastomer gel formula or desired characteristics 202, and forming or obtaining the elastomer gel preparation 203. Then a typical injection mold is created or obtained as described above that may or may not create transecting holes in the part 204. Molten elastomer gel containing uninitiated chemical foaming agent is then injected into the mold cavity and the part is cooled and removed from the cavity at temperatures that will not initiate the chemical foaming agent 205. The part is then introduced into an oven, with or without vacuum, at a temperature and for a duration that will allow the chemical foaming agent to initiate 206. The foamed part is actively cooled or permitted to cool 207. The foam is solid and non-flowable at room temperature and may be handled. Then the foam may be used as is or further processed 208 such as in a manufactured article, ending the process 209.

Figure 3:
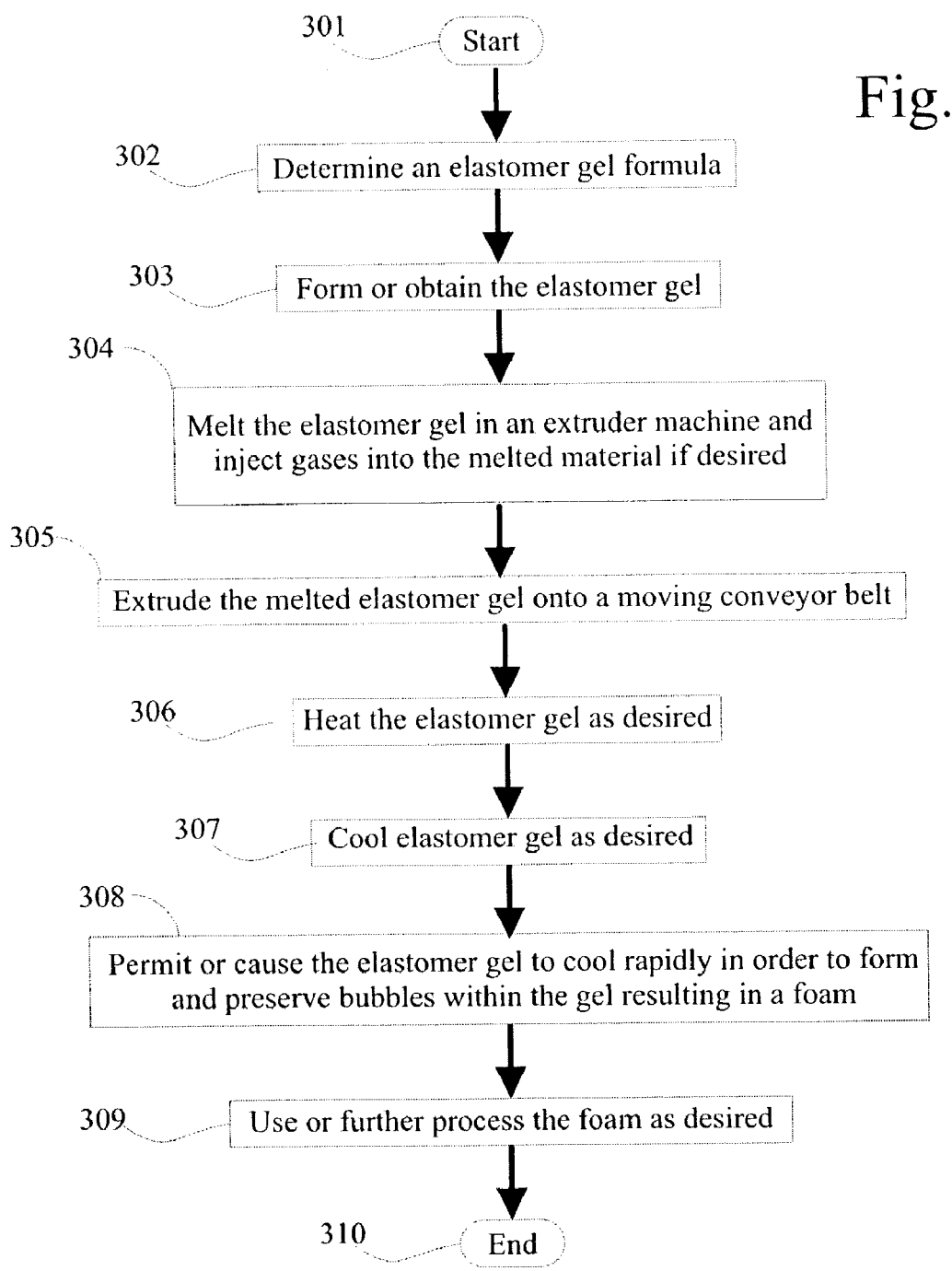

FIG. 3 depicts an example flow chart of steps that may be used in carrying out methods for making a foamed elastomer gel in bulk form as disclosed herein. Steps include start 301, determining an appropriate elastomer gel formula or desired characteristics 302, and forming or obtaining the elastomer gel preparation that may or may not include a chemical foaming agent 303. The elastomer gel preparation is then melted in an extruder machine and gases such as nitrogen or carbon dioxide are injected into the molten elastomer gel in conjunction in the presence or absence of a chemical foaming agent 304. The elastomer gel is then extruded onto a moving conveyor belt 305 and heated 306 or cooled 307 as desired. The molten elastomer gel is either actively cooled or permitted to cool 308 rapidly in order to solidify the gel, form a foam and preserve bubbles within the foam. The foam is solid and non-flowable at room temperature and may be handled. Then the foam may be used as is or further processed 309 such as in a manufactured article, ending 310 the process.

Elastomer gels used to make the devices may be of any desired softness or rigidity, but some examples will be in the durometer range of from less than 0 to about 50 on the Shore A scale. The manufacture of a gelatinous elastomer can be as disclosed in the patents and patent applications to which priority is claimed and may include any of melt blending, solvent blending or compounding by use of heat and pressure such as by using a single screw or twin screw compounding machine, or otherwise.

Elastomer Component

Compositions of elastomer gels maybe low durometer (as defined below) thermoplastic elastomeric compounds and visco-elastomeric compounds which include an elastomeric block copolymer component and a plasticizer component.

The elastomer component may include a triblock polymer of the general configuration A-B-A, wherein the A represents a crystalline polymer such as a monoalkenylarene polymer, including but not limited to polystyrene and functionalized polystyrene, and the B is an elastomeric polymer such as polyethylene, polybutylene, poly(ethylene/butylene), hydrogenated poly(isoprene), hydrogenated poly(butadiene), hydrogenated poly(isoprene+butadiene), poly(ethylene/propylene) or hydrogenated poly(ethylene/butylene+ethylene/propylene), or others. The A components of the material link to each other to provide strength, while the B components provide elasticity. Polymers of greater molecular weight are achieved by combining many of the A components in the A portions of each A-B-A structure and combining many of the B components in the B portion of the A-B-A structure, along with the networking of the A-B-A molecules into large polymer networks.

An example elastomer for making the elastomer gel material is a very high to ultra high molecular weight elastomer and oil compound having an extremely high Brookfield Viscosity (hereinafter referred to as "solution viscosity"). Solution viscosity is generally indicative of molecular weight. "Solution viscosity" is defined as the viscosity of a solid when dissolved in toluene at 25–30 degrees C., measured in centipoises (cps). "Very high molecular weight" is defined herein in reference to elastomers having a solution viscosity, 20 weight percent solids in 80 weight percent toluene, the weight percentages being based upon the total weight of the solution, from greater than about 20,000 cps to about 50,000 cps. An "ultra high molecular weight elastomer" is defined herein as an elastomer having a solution viscosity, 20 weight percent solids in 80 weight percent toluene, of greater than about 50,000 cps. Ultra high molecular weight elastomers have a solution viscosity, 10 weight percent solids in 90 weight percent toluene, the weight percentages being based upon the total weight of the solution, of about 800 to about 30,000 cps and greater. The solution viscosities, in 80 weight percent toluene, of the A-B-A block copolymers useful in the elastomer component of the gel are substantially greater than 30,000 cps. The solution viscosities, in 90 weight percent toluene, of the A-B-A elastomers useful in the elastomer component of the gel are in the range of about 2,000 cps to about 20,000 cps. Thus, the elastomer component of the gel material may have a very high to ultra high molecular weight.

The elastomeric B portion of the A-B-A polymers has an exceptional affinity for most plasticizing agents, including but not limited to several types of oils, resins, and others. When the network of A-B-A molecules is denatured, plasticizers which have an affinity for the B block can readily associate with the B blocks. Upon renaturation of the network of A-B-A molecules, the plasticizer remains highly associated with the B portions, reducing or even eliminating plasticizer bleed from the material when compared with similar materials in the prior art, even at very high oil: elastomer ratios. The reason for this performance may be any of the plasticization theories explained above (i.e., lubricity theory, gel theory, mechanistic theory, and free volume theory).

The elastomer used may be an ultra high molecular weight polystyrene-hydrogenated poly(isoprene+butadiene)-polystyrene, such as those sold under the brand names SEPTON® 4044, SEPTON® 4055 and SEPTON® 4077 by Kuraray, an ultra high molecular weight polystyrene-hydrogenated polyisoprene-polystyrene such as the elastomers made by Kuraray and sold as SEPTON® 2005 and SEPTON® 2006, or an ultra high molecular weight polystyrene-hydrogenated polybutadiene-polystyrene, such as that sold as SEPTON 8006 by Kuraray. High to very high molecular weight polystyrene-hydrogenated poly(isoprene+butadiene)-polystyrene elastomers, such as that sold under the trade name SEPTON® 4033 by Kuraray, are also useful in some formulations of the gel material because they are easier to process than the ultra high molecular weight elastomers due to their effect on the melt viscosity of the material.

Following hydrogenation of the midblocks of each of SEPTON® 4033, SEPTON® 4045, SEPTON® 4055, and SEPTON® 4077, less than about five percent of the double bonds remain. Thus, substantially all of the double bonds are removed from the midblock by hydrogenation.

SEPTON® 4055 has a very high molecular weight (approximately 300,000, as determined by Applicant's gel permeation chromatography testing). SEPTON® 4077 has a somewhat higher molecular weight, and SEPTON® 4045 has a somewhat lower molecular weight than SEPTON® 4055. Materials which include either SEPTON® 4045 or SEPTON® 4077 as the primary block copolymer typically have lower tensile strength than similar materials made with SEPTON® 4055.

Kuraray Co. Ltd. of Tokyo, Japan has stated that the solution viscosity of SEPTON® 4055, the most A-B-A triblock copolymer for use in gel material, 10% solids in 90% toluene at 25 degrees C., is about 5,800 cps. Kuraray also said that the solution viscosity of SEPTON 4055, 5% solids in 95% toluene at 25 degrees C., is about 90 cps. Although Kuraray has not provided a solution viscosity, 20% solids in 80% toluene at 25 degrees C., an extrapolation of the two data points given shows that such a solution viscosity would be about 400,000 cps. Applicant confirmed Kuraray's data by having an independent laboratory, SGS U.S. Testing Company Inc. of Fairfield, N.J., test the solution viscosity of SEPTON® 4055. When SGS attempted to dissolve 20% solids in 80% toluene at 25 degrees C., the resulting material did not resemble a solution. Therefore, SGS determined the solution viscosity of SEPTON 4055 using 10% solids in 90% toluene at 25 degrees C., which resulted in a 3,040 cps solution.

Other materials with chemical and physical characteristics similar to those of SEPTON® 4055 include other A-B-A triblock copolymers which have a hydrogenated midblock polymer that is made up of at least about 30% isoprene monomers and at least about 30% butadiene monomers, the percentages being based on the total number of monomers that make up the midblock polymer. Similarly, other A-B-A triblock copolymers which have a hydrogenated midblock polymer that is made up of at least about 30% ethylene/propylene monomers and at least about 30% ethylene/butylene monomers, the percentages being based on the total number of monomers that make up the midblock polymer, are materials with chemical and physical characteristics similar to those of SEPTON® 4055. Mixtures of block copolymer elastomers are also useful as the elastomer component of some of the formulations. In such mixtures, each type of block copolymer contributes different properties to the material. For example, high strength triblock copolymer elastomers are desired to improve the tensile strength and durability of a material. However, some high strength triblock copolymers are very difficult to process with some plasticizers. Thus, in such a case, block copolymer elastomers which improve the processability of the materials are desirable. In particular, the process of compounding SEPTON® 4055 with plasticizers may be improved via a lower melt viscosity by using a small amount of more flowable elastomer such as SEPTON® 8006, SEPTON® 2005, SEPTON® 2006, or SEPTON® 4033, to name only a few, without significantly changing the physical characteristics of the material.

In a second example of the usefulness of block copolymer elastomer mixtures in the gel materials, many block copolymers are not good compatibilizers. Other block copolymers readily form compatible mixtures, but have other undesirable properties. Thus, the use of small amount of elastomers which improve the uniformity with which a material mixes are desired. KRATON® G1701, manufactured by Shell Chemical Company of Houston, Tex., is one such elastomer that improves the uniformity with which the components of the gel material mix.

Many other elastomers, including but not limited to triblock copolymers and diblock copolymers are also useful in the elastomer gel. Applicant believes that elastomers having a significantly higher molecular weight than the ultra-high molecular weight elastomers useful in the elastomer gel material increase the softness thereof, but decrease the strength of the gel. Thus, high to ultra high molecular weight elastomers, as defined above, are desired for use in the gel material due to the strength of such elastomers when combined with a plasticizer.

Additives

Polarizable Plasticizer Bleed-Reducing Additives

Some of the elastomer gel materials described herein do not exhibit migration of plasticizers, even when placed against materials which readily exhibit a high degree of capillary action, such as paper, at room temperature. Gel materials with higher plasticizer to polymer ratios may exhibit migration (bleed) and a bleed reducing additive is helpful to address the bleed issue.

A plasticizer bleed-reducing additive that may be useful in the elastomer gel material includes hydrocarbon chains with readily polarizable groups thereon. Such polarizable groups include, without limitation, halogenated hydrocarbon groups, halogens, nitrites, and others. Applicant believes that the polarizability of such groups on the hydrocarbon molecule of the bleed-reducing additive have a tendency to form weak van der Waals bonding with the long hydrocarbon chains of the rubber portion of an elastomer and with the plasticizer molecules. Due to the great length of typical rubber polymers, several of the bleed-reducers will be attracted thereto, while fewer will be attracted to each plasticizer molecule. The bleed-reducing additives are believed to hold the plasticizer molecules and the elastomer molecules thereto, facilitating attraction between the elastomeric block and the plasticizer molecule. In other words, the bleed-reducing additives are believed to attract a plasticizer molecule at one polarizable site, while attracting an elastomeric block at another polarizable site, thus maintaining the association of the plasticizer molecules with the elastomer molecules, which inhibits exudation of the plasticizer molecules from the elastomer-plasticizer compound. Thus, each of the plasticizer molecules is attracted to an elastomeric block by means of a bleed-reducing additive.

The bleed-reducing additives may have a plurality of polarizable groups thereon, which facilitate bonding an additive molecule to a plurality of elastomer molecules and/or plasticizer molecules. It is believed that an additive molecule with more polarizable sites thereon will bond to more plasticizer molecules. Preferably, the additive molecules remain in a liquid or a solid state during processing of the gel material.

The bleed-reducing additives may be halogenated hydrocarbon additives such as those sold under the trade name DYNAMAR® PPA-791, DYNAMAR® PPA-790, DYNAMAR® FX-9613, and FLUORAD® FC 10 Fluorochemical Alcohol, each by 3M Company of St. Paul, Minn. Other additives are also useful to reduce plasticizer exudation from the gel material. Such additives include, without limitation, other halogenated hydrocarbons sold under the trade name FLUORAD®, including without limitation FC-129, FC-135, FC-430, FC-722, FC-724, FC-740, FX-8, FX-13, FX-14 and FX-189; halogentated hydrocarbons such as those sold under the trade name ZONY®, including without limitation FSN 100, FSO 100, PFBE, 8857A, BA-L, BA-N, TBC and FTS, each of which are manufactured by du Pont of Wilmington, Del.; halogenated hydrocarbons sold under the trade name EMCOL by Witco Corp of Houston, Tex., including without limitation 4500 and DOSS; other halogenated hydrocarbons sold by 3M under the trade name DYNAMAR®.; chlorinated polyethylene elastomer (CPE), distributed by Harwick, Inc. of Akron, Ohio; chlorinated paraffin wax, distributed by Harwick, Inc.; and others. The bleed reducing additives may be hydrocarbon resins, elastomeric diblock copolymers, polyisobutylene, butyl rubber, or transpolyoctenylene rubber ("tor rubber").

Detackifiers

The elastomer gel may include a detackifier. Tack is not necessarily desired. However, some of the elastomer gel formulas impart tack to the media. Soaps, detergents and other surfactants have detackifying abilities and are useful in the gel material. "Surfactants," as defined herein, refers to soluble surface active agents which contain groups that have opposite polarity and solubilizing tendencies. Surfactants form a monolayer at interfaces between hydrophobic and hydrophilic phases; when not located at a phase interface, surfactants form micelles. Surfactants have detergency, foaming, wetting, emulsifying and dispersing properties. Sharp, D. W. A., DICTIONARY OF CHEMISTRY, 381–82 (Penguin, 1990). For example, coco diethanolamide, a common ingredient in shampoos, is useful in the gel material as a detackifying agent. Coco diethanolamide resists evaporation, is stable, relatively non-toxic, non-flammable and does not support microbial growth. Many different soap or detergent compositions could be used in the material as well. Other detackifiers include glycerin, epoxidized soybean oil, dimethicone, tributyl phosphate, block copolymer polyether, hydrocarbon resins, polyisobutylene, butyl rubber, diethylene glycol mono oleate, tetraethyleneglycol dimethyl ether, and silicone, to name only a few. Glycerine is available from a wide variety of sources. Witco Corp. of Greenwich, Conn. sells epoxidized soybean oil as DRAPEX®. Dimethicone is available from a variety of vendors, including GE Specialty Chemicals of Parkersburg, W. Va. under the trade name GE SF 96-350. C. P. Hall Co. of Chicago, Ill. markets block copolymer polyether as PLURONIC L-61. C. P. Hall Co. also manufactures and markets diethylene glycol mono oleate under the name Diglycol Oleate—Hallco CPH-I-SE. Other emulsifiers and dispersants are also useful in the gel material. Tetraethyleneglycol dimethyl ether is available under the trade name TETRAGLYME® from Ferro Corporation of Zachary, La. Applicant believes that TETRAGLYME® also reduces plasticizer exudation from the gel material.

Antioxidants

The elastomer gel material may also include additives such as an antioxidant. Antioxidants such as those sold under the trade names IRGANOX® 1010 and IRGAFOS® 168 by Ciba-Geigy Corp. of Tarrytown, N.Y. are useful by themselves or in combination with other antioxidants. Antioxidants protect the gel materials against thermal degradation during processing, which requires or generates heat. In addition, antioxidants provide long term protection from free radicals. An antioxidant inhibits thermo-oxidative degradation of the compound or material to which it is added, providing long term resistance to polymer degradation. Heat, light (in the form of high energy radiation), mechanical stress, catalyst residues, and reaction of a material with impurities all cause oxidation of the material. In the process of oxidation, highly reactive molecules known as free radicals are formed and react in the presence of oxygen to form peroxy free radicals, which further react with organic material (hydro-carbon molecules) to form hydroperoxides. The two major classes of antioxidants are the primary antioxidants and the secondary antioxidants. Peroxy free radicals are more likely to react with primary antioxidants than with most other hydrocarbons. In the absence of a primary antioxidant, a peroxy free radical would break a hydrocarbon chain. Thus, primary antioxidants deactivate a peroxy free radical before it has a chance to attack and oxidize an organic material. Most primary antioxidants are known as sterically hindered phenols. One example of sterically hindered phenol is marketed by Ciba-Geigy as IRGANOX® 1010, which has the chemical name 3,5-bis(1,1-dimethylethyl)-4-hydroxybenzenepropanoic acid, 2,2-bis [[3-[3,5-bis (dimethylethyl)-4-hydroxyphenyl]-1-oxopropoxy]methyl]1, 3-propa nediyl ester. The FDA refers to IRGANOX® 1010 as tetrakis[methylene(3,5-di-tert-butyl-4-hydroxyhydrocinnimate)]methane. Other hindered phenols are also useful as primary antioxidants in the material. Similarly, secondary antioxidants react more rapidly with hydroperoxides than most other hydrocarbon molecules. Secondary antioxidants have been referred to as hydroperoxide decomposers. Thus, secondary antioxidants protect organic materials from oxidative degradation by hydroperoxides.

Commonly used secondary antioxidants include the chemical classes of phosphites/phosphonites and thioesters, many of which are useful in the gel material. The hydroperoxide decomposer can be a phosphite known as Tris(2,4-di-tert-butylphenyl)phosphite and marketed by Ciba-Geigy as IRGAFOS® 168. Primary and secondary antioxidants form synergistic combinations to ward off attacks from both peroxy free radicals and hydroperoxides. Other antioxidants, including but not limited to multi-functional antioxidants, are also useful in the material. Multifunctional antioxidants have the reactivity of both a primary and a secondary antioxidant. IRGANOX® 1520 D, manufactured by Ciba-Geigy is one example of a multifunctional antioxidant. Vitamin E antioxidants, such as that sold by Ciba-Geigy as IRGANOX® E17, are also useful in the gel material.

The elastomer gel material may include up to about three weight percent antioxidant, based on the weight of the elastomer component, when only one type of antioxidant is used. The material may include as little as 0.1 weight percent of an antioxidant, or no antioxidant at all. When a combination of antioxidants is used, each may comprise up to about three weight percent, based on the weight of the elastomer component. Additional antioxidants may be added for severe processing conditions involving excessive heat or long duration at a high temperature.

The use of excess antioxidants reduces or eliminates tack on the exterior surface of the gel material. Excess antioxidants appear to migrate to the exterior surface of the material following compounding of the material. Such apparent migration occurs over substantial periods of time, from hours to days or even longer.

Flame Retardants

Flame retardants may also be added to elastomer gel materials. Flame retardants include but are not limited to diatomaceous earth flame retardants sold as GREAT LAKES DE 83R and GREAT LAKES DE 79 by Great Lakes Filter, Division of Acme Mills Co. of Detroit, Mich. Most flame retardants that are useful in elastomeric materials are also useful in the gel material.

Chemical blowing agents, such as SAFOAM® FP-40, manufactured by Reedy International Corporation of Keyport, N.J. and others are useful for making a gel medium that is self-extinguishing.

Colorants

Colorants may also be used in gel materials. Any colorant which is compatible with elastomeric materials may be used. Aluminum lake colorants such as those manufactured by Warner Jenkinson Corp. of St. Louis, Mo. Are available. Pigments manufactured by Day Glo Color Corp. of Cleveland, Ohio; Lamp Black, such as that sold by Spectrum Chemical Manufacturing Corp. of Gardena, Calif.; and Titanium Dioxide (white) are also available. By using these colorants, the gel material takes on intense shades of colors, including but not limited to pink, red, orange, yellow, green, blue, violet, brown, flesh, white and black.

Paint

The elastomer gel may also be painted.

Other Additives

Melt temperature modifiers useful in the gel include cross-linking agents, hydrocarbon resins, diblock copolymers of the general configuration A-B and triblock copolymers of the general configuration A-B-A wherein the end block A polymers include functionalized styrene monomers, and others.

Melt viscosity modifiers that tend to reduce the melt viscosity of the pre-compounded component mixture of the medium include hydrocarbon resins, transpolyoctenylene rubber, castor oil, linseed oil, non-ultra high molecular weight thermoplastic rubbers, surfactants, dispersants, emulsifiers, and others.

Melt viscosity modifiers that tend to increase the melt viscosity of the pre-compounded component mixture of the gel material include hydrocarbon resins, butyl rubber, polyisobutylene, additional triblock copolymers having the general configuration A-B-A and a molecular weight greater than that of each of the block copolymers in the elastomeric block copolymer component of the material, particulate fillers, microspheres, butadiene rubber, ethylene/propylene rubber, ethylene/butylene rubber, and others.

Tensile strength modifiers which tend to increase the tensile strength of the gel material for use in the gel material include mid block B-associating hydrocarbon resins, non-end-block solvating hydrocarbon resins which associate with the end blocks, particulate reinforcers, and others.

Shrinkage inhibitors, which tend to reduce shrinkage of the gel material following compounding, that are useful in the material include hydrocarbon resins, particulate fillers, microspheres, transpolyoctenylene rubber, and others.

Microspheres

Microspheres may also be added to the gel material. The gel material may contain up to about 90% microspheres, by volume. In one microsphere-containing formulation of the gel material, microspheres make up at least about 30% of the total volume of the material. A second microsphere-containing formulation of the gel material includes at least about 50% microspheres, by volume.

Different types of microspheres contribute various properties to the material. For example, hollow acrylic microspheres, such as those marketed under the brand name MICROPEARL®, and generally in the 20 to 200 micron size range, by Matsumoto Yushi-Seiyaku Co., Ltd. of Osaka, Japan, lower the specific gravity of the material. In other formulations of the gel, the microspheres may be unexpanded DU(091-80), which expand during processing of the gel material, or pre-expanded DE (091-80) acrylic microspheres from Expancel Inc. of Duluth, Ga.

In formulations of the material which include hollow acrylic microspheres, the microspheres have substantially instantaneous rebound when subjected to a compression force which compresses the microspheres to a thickness of up to about 50% of their original diameter or less.

Hollow microspheres also decrease the specific gravity of the gel material by creating gas pockets therein. When a gel material includes microspheres, the microspheres must be dispersed, on average, at a distance of about one-and-a-half (1.5) times the average microsphere diameter or a lesser distance from one another in order to achieve a specific gravity of less than about 0.50. Other formulations of the gel material have specific gravities of less than about 0.65, less than about 0.45, and less than about 0.25.

MICROPEARL® and EXPANCEL® acrylic microspheres are because of their highly flexible nature, as explained above, which tend to not restrict deformation of the thermoplastic elastomer. Glass, ceramic, and other types of microspheres may also be used in the thermoplastic gel material.

Plasticizer Component

As explained above, plasticizers allow the midblocks of a network of triblock copolymer molecules to move past one another. Thus, Applicant believes that plasticizers, when trapped within the three dimensional web of triblock copolymer molecules, facilitate the disentanglement and elongation of the elastomeric midblocks as a load is placed on the network. Similarly, Applicant believes that plasticizers facilitate recontraction of the elastomeric midblocks following release of the load. The plasticizer component of the gel may include oil, resin, a mixture of oils, a mixture of resins, other lubricating materials, or any combination of the foregoing.

Oils

The plasticizer component of the gel material may include a commercially available oil or mixture of oils. The plasticizer component may include other plasticizing agents, such as liquid oligomers and others, as well. Both naturally derived and synthetic oils are useful in the gel material. The oils may have a viscosity of about 70 SUS to about 500 SUS at about 100 degrees F. Paraffinic white mineral oils having a viscosity in the range of about 90 SUS to about 200 SUS at about 100 degrees F. may be used One embodiment of a plasticizer component of the gel includes paraffinic white mineral oils, such as those having the brand name DUOPRIME®, by Lyondell Lubricants of Houston, Tex., and the oils sold under the brand name TUFFLO® by Witco Corporation of Petrolia, Pa. For example, the plasticizer component of the gel may include paraffinic white mineral oil such as that sold under the trade name LP-150 by Witco.

Paraffinic white mineral oils having an average viscosity of about 90 SUS, such as DUOPRIME® 90, are used in other embodiments of the plasticizer component. Applicant has found that DUOPRIME® 90 and oils with similar physical properties can be used to impart the greatest strength to the gel material.

Other oils are also useful as plasticizers in compounding the gel material. Examples of representative commercially available oils include processing oils such as paraffinic and naphthenic petroleum oils, highly refined aromatic-free or low aromaticity paraffinic and naphthenic food and technical grade white petroleum mineral oils, and synthetic liquid oligomers of polybutene, polypropene, polyterpene, etc., and others. The synthetic series process oils are oligomers which are permanently fluid liquid non-olefins, isoparaffins or paraffins. Many such oils are known and commercially available.

Examples of representative commercially available oils include Amoco.RTM. polybutenes, hydrogenated polybutenes and polybutenes with epoxide functionality at one end of the polybutene polymer. Examples of various commercially available oils include: Bayol, Bernol, American, Blandol, Drakeol, Ervol, Gloria, Kaydol, Litetek, Marcol, Parol, Peneteck, Primol, Protol, Sontex, and the like.

Resins

Resins useful in the plasticizer component include, but are not limited to, hydrocarbon-derived and rosin-derived resins having a ring and ball softening point of up to about 150 degrees C., or from about 0 degrees C. to about 25 degrees C., and a weight average molecular weight of at least about 300.

Resins or resin mixtures which are highly viscous flowable liquids at room temperature (about 23 degrees C.) may be used. Plasticizers which are fluid at room temperature impart softness to the gel material. Resins which are not flowable liquids at room temperature are also useful in the material.

Some resins used have a ring and ball softening point of about 18 degrees C.; melt viscosities of about 10 poises (ps) at about 61 degrees C., about 100 ps at about 42 degrees C. and about 1,000 ps at about 32. degrees C. One such resin is marketed as REGALREZ® 1018 by Hercules Incorporated of Wilmington, Del. Variations of REGALREZ® 1018 which are useful in the material have viscosities including, but not limited to, 1025 stokes, 1018 stokes, 745 stokes, 114 stokes, and others.

Room temperature flowable resins that are derived from poly-.beta.-pinene and have softenening points similar to that of REGALREZ® 1018 are also useful in the plasticizer component of the medium. One such resin, sold as PICCOLYTE® S25 by Hercules Incorporated, has a softening point of about 25 degrees C.; melt viscosities of about 10 ps at about 80 degrees C., about 100 ps at about 56 degrees C. and about 1,000 ps at about 41 degrees C.; a MMAP value of about 88 degrees C.; a DACP value of about 45 degrees C.; an OMSCP value of less than about −50. degrees C. Other PICCOLYTE® resins may also be used in the gel material.

Another room temperature flowable resin which is useful in the plasticizer component of the material is marketed as ADTAC® LV by Hercules Incorporated. That resin has a ring and ball softening point of about 5 degrees C.; melt viscosities of about 10 ps at about 62 degrees C., about 100 ps at about 36 degrees C. and about 1,000 ps at about 20 degrees C.; a MMAP value of about 93 degrees C.; a DACP value of about 44 degrees C.; an OMSCP value of less than about −40 degrees C.

Resins such as the liquid aliphatic C-5 petroleum hydrocarbon resin sold as WINGTACK® 10 by the Goodyear Tire & Rubber Company of Akron, Ohio and other WINGTACK® resins are also useful in the gel material. WINGTACK® 10 has a ring and ball softening point of about 10 degrees C.; a Brookfield Viscosity of about 30,000 cps at about 25 degrees C.; melt viscosities of about 10 ps at about 53 degrees C. and about 100 ps at about 34 degrees C.; a 1:1 polyethylene-to-resin ratio cloud point of about 89 degrees C.; a 1:1 microcrystalline wax-to-resin ratio cloud point of about 77 degrees C.; and a 1:1 paraffin wax-to-resin ratio cloud point of about 64 degrees C.

Resins that are not readily flowable at room temperature (i.e., are solid, semi-solid, or have an extremely high viscosity) or that are solid at room temperature are also useful in the gel material. One such solid resin is an aliphatic C-5 petroleum hydrocarbon resin having a ring and ball softening point of about 98 degrees C.; melt viscosities of about 100 ps at about 156 degrees C. and about 1000 ps at about 109 degrees C.; a 1:1 polyethylene-to-resin ratio cloud point of about 90 degrees C.; a 1:1 microcrystalline wax-to-resin ratio cloud point of about 77 degrees C.; and a 1:1 paraffin wax-to-resin ratio cloud point of about 64 degrees C. Such a resin is available as WINGTACK® 95 and is manufactured by Goodyear Chemical Co.

Polyisobutylene polymers are an example of resins which are not readily flowable at room temperature and that are useful in the gel material. One such resin, sold as VISTANEX®

LM-MS by Exxon Chemical Company of Houston, Tex., has a Tg of −60. degrees C., a Brookfield Viscosity of about 250 cps to about 350 cps at about 350 degrees F., a Flory molecular weight in the range of about 42,600 to about 46,100, and a Staudinger molecular weight in the range of about 10,400 to about 10,900. The Flory and Staudinger methods for determining molecular weight are based on the intrinsic viscosity of a material dissolved in diisobutylene at 20 degrees C.

Glycerol esters of polymerized rosin are also useful as plasticizers in the gel material. One such ester, manufactured and sold by Hercules Incorporated as HERCULES® Ester Gum 10D Synthetic Resin, has a softening point of about 116 degrees C.

Many other resins are also suitable for use in the gel material. In general, plasticizing resins are those which are compatible with the B block of the elastomer used in the material, and non-compatible with the A blocks.

In some formulations, tacky materials may be desirable. In such formulations, the plasticizer component of the gel material may include about 20 weight percent or more, about 40 weight percent or more, about 60 weight percent or more, or up to about 100 weight percent, based upon the weight of the plasticizer component, of a tackifier or tackifier mixture.

Plasticizer Mixtures

The use of plasticizer mixtures in the plasticizer component of the gel material is useful for tailoring the physical characteristics of the gel material. For example, characteristics such as durometer, tack, tensile strength, elongation, melt flow and others may be modified by combining various plasticizers.

For example, a plasticizer mixture which includes at least about 37.5 weight percent of a paraffinic white mineral oil having physical characteristics similar to those of LP-150 (a viscosity of about 150 SUS at about 100 degrees F., a viscosity of about 30 centistokes (cSt) at about 40 degrees C., and maximum pour point of about −35 degrees F.) and up to about 62.5 weight percent of a resin having physical characteristics similar to those of REGALREZ® 1018 (such as a softening point of about 20 degrees C.; a MMAP value of about 70 degrees C.; a DACP value of about 15 degrees C.; an OMSCP value of less than about −40 degrees C.; all weight percentages being based upon the total weight of the plasticizer mixture, could be used in a gel. When compared to a material plasticized with the same amount of an oil such as LP-150, the material which includes the plasticizer mixture has decreased oil bleed and increased tack.

When resin is included with oil in a plasticizer mixture of the gel the material exhibits reduced oil bleed. For example, a formulation of the material which includes a plasticizing component which has about three parts plasticizing oil (such as LP-150), and about five parts plasticizing resin (such as REGALREZ® 1018) exhibits infinitesimal oil bleed at room temperature, if any, even when placed against materials with high capillary action, such as paper.

The plasticizer:block copolymer elastomer ratio, by total combined weight of the plasticizer component and the block copolymer elastomer component in some formulations ranges from as low as about 1:1 or less to higher than about 25:1. In applications where plasticizer bleed is acceptable, the ratio may as high as about 100:1 or more. Plasticizer:block copolymer ratios in the range of about 2.5:1 to about 8:1 may be more common. A ratio such as 5:1 provides the desired amounts of rigidity, elasticity and strength for many typical applications. A plasticizer to block copolymer elastomer ratio of 2.5:1 has a high amount of strength and elongation.

Compounding Methods

Compounding may be carried out by melt blending, solvent blending, or compounding under heat and pressure such as by use of a single screw or twin screw compounding machine.

While the devices, materials and methods have been described and illustrated in conjunction with a number of specific examples, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations of lights described herein are to be considered in all respects as only illustrative, and not restrictive. All changes that come within the meaning and range of equivalency of the claims are to be embraced within their scope.

The invention claimed is:

1. A method for forming a foamed elastomer gel comprising the steps of:
   obtaining an elastomer gel,
   obtaining a mold for forming the elastomer gel in to a foam,
   the mold having an internal cavity suitable for forming said elastomer gel therein, the mold including tubes that transect the mold cavity,
   said tubes having the ability to be heated or cooled by fluid, heat conduction, or electrical resistance,
   causing said elastomer gel to be present in said cavity in a molten state,
   introducing pressurized gas into said molten elastomer gel,
   achieving bubble formation and stability in said elastomer gel by varying the temperature of said tubes,
   permitting said elastomer gel to solidify as a foam with bubbles present within it,
   withdrawing said tubes from said mold, followed by removing a foamed gel from said cavity.

2. A method as recited in claim 1 wherein said foamed elastomer gel is solid and non-flowable at room temperature.

3. A method as recited in claim 1 wherein 4 said foamed elastomer gel is greater than 4 mm thick.

4. A method as recited in claim 1 wherein said foamed elastomer gel is greater than 4 mm thick and less than 1.5 meter thick.

5. A method as recited in claim 1 wherein said foamed elastomer gel has a generally even distribution of gas bubbles within it.

6. A method as recited in claim 1 wherein wherein said gas bubbles are created by chemical foaming agents.

7. A method as recited in claim 1 wherein said gas bubbles are created by injecting gas into the melted elastomer gel at very high pressure before being formed into the desired shape.

8. A method as recited in claim 1 said elastomer gel formula includes an elastomer and a plasticizer.

9. A method as recited in claim 1 wherein wherein said elastomer is an A-B-A triblock copolymer.

10. A method as recited in claim 1 wherein said elastomer is selected from the group consisting of SEPS, SEBS and SEEPS.

11. A method as recited in claim 10 wherein wherein said plasticizer is selected from the group consisting of resin, rosin and oil.

12. A method as recited in claim 10 wherein said elastomer gel formula includes:
    an elastomer,
    said elastomer being an A-B-A triblock copolymer,
    said A-B-A triblock copolymer being selected from the group consisting of SEPS, SEBS and SEEPS, and
    a plasticizer,
    said plasticizer being selected from the group consisting of resin, rosin and oil.

13. A method as recited in claim 12 further comprising a component selected from the group consisting of antioxidants, colorants, bleed reducing additives, and microspheres.

14. A method as recited in claim 12 further comprising adding an emulsifier to said elastomer gel for the purpose of improving the characteristics of a finished foam resulting from the method.

15. A method as recited in claim 12 further comprising adding a stability-inducing additive to said elastomer gel for the purpose of improving stability in bubble distribution in the molten elastomer gel.

16. A method as recited in claim 15 wherein said stability-inducing additive is selected from the group consisting of fatty acids, stearamides, and stearyl stearamides.

17. A method as recited in claim 12 further comprising adding a surfactant to said elastomer gel for the purpose of achieving improved bubble stability in the molten gel.

18. A method as recited in claim 17 wherein said surfactant is selected from the group consisting of Zonyl FSG, aliphatic carboxylic acids such as lauric acid, myristic acid, palmitic acid, stearic acid, and oleic acid; fatty acid soaps such as sodium salts or potassium salts of the above aliphatic carboxylic acids; N-acyl-N-methylglycine salts, N-acyl-N-methyl-.beta.-alanine salts, N-acylglutamic acid salts, polyoxyethylene alkyl ether carboxylic acid salts, acylated peptides, alkylbenzenesulfonic acid salts, alkylnaphthalenesulfonic acid salts, naphthalenesulfonic acid salt-formalin polycondensation products, melaminesulfonic acid salt-formalin polycondensation products, dialkylsulfosuccinic acid ester salts, alkyl sulfosuccinate disalts, polyoxyethylene alkylsulfosuccinic acid disalts, alkylsulfoacetic acid salts, .alpha.-olefinsulfonic acid salts, N-acylmethyltaurine salts, sodium dimethyl 5-sulfoisophthalate, sulfated oil, higher alcohol sulfuric acid ester salts, polyoxyethylene alkyl ether sulfuric acid salts, secondary higher alcohol ethoxysulfates, polyoxyethylene alkyl phenyl ether sulfuric acid salts, monoglysulfate, sulfuric acid ester salts of fatty acid alkylolamides, polyoxyethylene alkyl ether phosphoric acid salts, polyoxyethylene alkyl phenyl ether phosphoric acid salts, alkyl phosphoric acid salts, sodium alkylamine oxide bistridecylsulfosuccinates, sodium dioctylsulfosuccinate, sodium dihexylsulfosuccinate, sodium dicyclohexylsulfosuccinate, sodium diamylsulfosuccinate, sodium diisobutylsulfosuccinate, alkylamine guanidine polyoxyethanol, disodium sulfosuccinate ethoxylated alcohol half esters, disodium sulfosuccinate ethoxylated nonylphenol half esters, disodium isodecylsulfosuccinate, disodium N-octadecylsulfosuccinamide, tetrasodium N-(1,2-dicarboxyethyl)-N-octadecylsulfosuccinamide, disodium mono- or didodecyldiphenyl oxide disulfonates, sodium diisopropylnaphthalenesulfonate, and neutralized condensed products from sodium naphthalenesulfonate.

19. A method as recited in claim 1 further comprising applying a vacuum to said elastomer gel to influence formation of a foamed gel.

20. A method as recited in claim 1 wherein said molten elastomer gel is formed to the desired shape by injecting, extruding, pumping, or otherwise causing the material to enter into a mold with a cavity of the desired shape.

21. A method as recited in claim 20 wherein said mold has the ability to be heated and/or cooled by fluid or by other means.

22. A method as recited in claim 20 wherein a vacuum is applied to the mold cavity to improve the resulting elastomer gel foam.

23. A method as recited in claim 20 wherein the molten elastomer gel is controlled to a temperature sufficiently high to initiate any chemical foaming agents in the formulation.

24. A method as recited in claim 20 wherein the molten elastomer gel is controlled to a temperature sufficiently high to allow the elastomer gel to permanently deform as the gas bubbles initiate and grow.

25. A method as recited in claim 20 wherein the molten elastomer gel is controlled to a temperature sufficiently low to prevent the gas bubbles of the desired size and distribution from migrating out of the elastomer gel and to prevent said gas bubbles from joining into larger gas bubbles.

26. A method as recited in claim 20 wherein the desired gas bubbles are formed by incorporating a chemical foaming agent in the elastomer gel formulation.

27. A method as recited in claim 20 wherein the molten elastomer gel is cooled rapidly to prevent the gas bubbles of the desired size and distribution from migrating out of the elastomer gel and to prevent said gas bubbles from joining into larger gas bubbles.

28. A method as recited in claim 20 wherein the desired gas bubbles are formed by injecting gas into the melted elastomer gel at high pressure when it is molten.

29. A method as recited in claim 28 wherein the gas is injected into the molten material in an extruder machine.

30. A method as recited in claim 28 wherein the gas is injected into the molten material in a pump.

31. A method as recited in claim 1 wherein the foamed elastomer gel is removed from the mold in a direction that is parallel to said tubes or rods.

32. A method as recited in claim 1 wherein said elastomer gel is formed to the desired shape by injecting said molten elastomer gel containing chemical foaming agents into a mold at a temperature sufficiently low that said chemical foaming agent is not initiated and removing said part from said cavity at a temperature sufficiently low that the part can be handled without deformation.

33. A method as recited in claim 32 wherein said molded part is heated in an oven at a temperature sufficiently high to initiate the chemical foaming agent.

34. A method as recited in claim 32 wherein said molded part is placed in an oven at a temperature sufficiently high to initiate the chemical foaming agent and a vacuum is applied to said oven.

35. A method as recited in claim 32 wherein said molded part is heated in an oven at a temperature sufficiently high to allow the elastomer gel to permanently deform as the gas bubbles initiate and grow.

36. A method as recited in claim 32 wherein said molded part is placed in an oven at a temperature sufficiently high to allow the elastomer gel to permanently deform as the gas bubbles initiate and grow and a vacuum is applied to said oven.

37. A method as recited in claim 1 wherein said molten elastomer gel is formed to the desired shape by extruding, pumping, or otherwise causing the material to be placed upon a moving conveyor belt at the desired height and width.

38. A method as recited in claim 37 wherein said elastomer gel is heated in an oven at a temperature sufficiently high to initiate any chemical foaming agents in the formulation.

39. A method as recited in claim 37 wherein said elastomer gel is placed in an oven at a temperature sufficiently high to initiate any chemical foaming agent in the formulation and a vacuum is applied to said oven.

40. A method as recited in claim 37 wherein said elastomer gel is heated in an oven at a temperature sufficiently high to allow the elastomer gel to permanently deform as the gas bubbles initiate and grow.

41. A method as recited in claim 37 wherein said elastomer gel is placed in an oven at a temperature sufficiently high to allow the to permanently deform as the gas bubbles initiate and grow and a vacuum is applied to said oven.

42. A method as recited in claim 37 wherein the desired gas bubbles are formed by injecting gas into the melted elastomer gel at high pressure when it is molten.

43. A method as recited in claim 42 wherein the gas is injected into the molten material in an extruder machine.

44. A method as recited in claim 42 wherein the gas is injected into the molten material in a pump.

45. A method as recited in claim 37 wherein the desired gas bubbles are formed by incorporating a chemical foaming agent in the elastomer gel formulation.

* * * * *